United States Patent [19]
Whitt

[11] Patent Number: 5,359,196
[45] Date of Patent: Oct. 25, 1994

[54] MASS SPECTROMETRY WITH GAS COUNTERFLOW FOR PARTICLE BEAM

[75] Inventor: Robert T. Whitt, Carrollton, Tex.

[73] Assignee: Hewlett-Packard Company, Palo Alto, Calif.

[21] Appl. No.: 66,369

[22] Filed: May 24, 1993

[51] Int. Cl.$^5$ .............................................. H01J 49/04
[52] U.S. Cl. .................................... 250/288; 250/281; 250/282
[58] Field of Search ............... 250/288 R, 288 A, 281, 250/282, 285, 289; 210/656, 198.2

[56] References Cited

U.S. PATENT DOCUMENTS

| | | | |
|---|---|---|---|
| 4,137,750 | 2/1979 | French et al. | 250/228 R |
| 4,531,056 | 7/1985 | Labowsky et al. | 250/282 |
| 4,861,988 | 8/1989 | Henion et al. | 250/228 A |
| 4,883,958 | 11/1989 | Vestal | 250/288 A |
| 4,885,076 | 12/1989 | Smith et al. | 250/288 R |
| 4,958,529 | 9/1990 | Vestal | 250/288 |
| 4,977,320 | 12/1990 | Chowdhury et al. | 250/288 |
| 5,122,670 | 6/1992 | Mylchreest et al. | 250/282 |
| 5,266,192 | 11/1993 | Ligon et al. | 250/288 A |

OTHER PUBLICATIONS

Apffel, Alex, "Environmental Applications of Magic LC/MS" *Proceedings of the Third Annual United States Environmental Protection Agency Symposium on Solid Waste Testing and Quality Assurance,* vol. II, Jul., 1987, Washington, D.C., pp. 6-119-6-136.

Willoughby, Ross C. and Richard F. Browner, "Monodisperse Aerosol Generation Interface for Combining Liquid Chromatography with Mass Spectroscopy", *Analytical Chemistry,* vol. 56, No. 14, Dec. 1984, pp. 2626-2631.

"Presenting the MS Engine", Publication No. 23-59-53-4760 by Hewlett-Packard Company, Apr., 1990.

"HP Particle Beam LC/MS . . . it makes LC/MS as practical as GC/MS", Publication No. 23-5956-4133 by Hewlett-Packard Company, Jun., 1988.

*Primary Examiner*—Paul M. Dzierzynski
*Assistant Examiner*—James Beyer

[57] ABSTRACT

In an LC mode, the GC system of a GC/LC/MS system provides a counterflow to an LC particle beam. The counterflow increases signal strength and, for some relatively high molecular mass analytes, reduces fragmentation.

7 Claims, 3 Drawing Sheets

MASS SPECTROMETRY WITH GAS COUNTERFLOW FOR PARTICLE BEAM

BACKGROUND OF THE INVENTION

The present invention relates to mass spectrometry and, more particularly, to a system and method in which a particle beam is introduced into a mass spectrometer for analysis. A major objective of the present invention is to provide for a stronger signal strength in the mass analyzer output.

GC/LC/MS systems, which combine gas chromatography (GC), liquid chromatography (LC) and mass spectrometry (MS), are used for several purposes including 1) environmental studies, for example, to evaluate water, soil, and waste; 2) food analysis, to identify contaminants and adulterants; 3) pharmaceutical development, to analyze natural and synthetic products; and 4) life sciences, to characterize protein components.

Chromatography includes a class of separation techniques in which, at any given time during separation, some molecules of a component are adsorbed to a stationary solid support, while other molecules are carried by a mobile fluid. The adsorbed molecules are said to be in a "stationary phase" while the fluid-borne molecules are said to be in a "mobile phase".

At equilibrium, the rate at which a component's molecules in the stationary phase are released to the mobile phase equals the rate at which the same component's molecules in the mobile phase are adsorbed to the stationary phase. For each component, the ratio of the number of molecules in the stationary phase to the number of molecules in the mobile phase is quantified by a partitioning coefficient. This partitioning coefficient thus corresponds to the average percentage of time the molecules of a component are in the mobile phase. This percentage correlates with the mobility of the component past the solid support. Sample components with different mobilities separate, as they progress past the solid support. With sufficient separation, the components emerge serially in the chromatography effluent.

Both liquid chromatography and gas chromatography systems are known. In liquid chromatography, the fluid can be an organic liquid solvent, an aqueous liquid solvent, or a mixture of organic and aqueous solvents. In gas chromatography, the fluid can be a carrier gas. The effluent is, of course, liquid in the LC case, and gaseous in the GC case. GC tends to be preferred for volatile components, while LC provides a complementary alternative for nonvolatile components.

To complete the analysis of a sample mixture, the eluting components need to be identified and quantified. Mass spectrometers provide for fast, sensitive, high-resolution identification and quantification. A mass spectrometer provides a mass spectrum of a sample component by filtering sample subcomponents according to molecular mass and quantifying the number of subcomponent molecules at each molecular mass.

A typical mass spectrometer accepts a particle beam input, the particles of the beam being analyte molecules. The mass spectrometer includes an ion source that is activated to ionize the analyte molecule and form an ion beam. The ion beam is then sweep-filtered according to charge-to-mass ratio. The mass spectrometer can include an electron multiplier to detect and quantify the swept ion beam output. The time-varying output of the electron multiplier is a mass spectrum of concentration as a function of charge-to-mass ratio.

The output of a gas chromatography column is a particle-beam of carrier gas and gaseous analyte molecules. Generally, the GC particle-beam is compatible with the mass spectrometer, so no specialized GC/MS interface is required. However, when a GC packed column is used, a gas jet separator can be used to remove the bulk of the carrier gas. The GC particle-beam entering the mass spectrometer is ionized and mass analyzed.

The liquid output of the LC system is not directly compatible with the requirements for ionization and the vacuum conditions of the mass spectrometer. Accordingly, LC/MS interfaces can include a particle-beam generator that converts liquid effluent into a particle beam. A typical particle-beam generator comprises a nebulizer gas source, a nebulizer, a desolvation chamber, a momentum separator, and a transfer probe. In the nebulizer, the LC effluent is joined by a stream of helium and converted into an aerosol of uniform droplets. Solvent is vaporized as the droplets traverse the desolvation chamber, freeing sample particles.

The sample particles proceed as a beam through a momentum separator. Vacuum pumps maintain the momentum separator at a lower pressure than the desolvation chamber. The vacuum pumps divert throughgoing particles laterally, drawing lower momentum helium and solvent vapor into the vacuum exhaust system. The higher momentum sample particles remain in a particle beam that enters the mass spectrometer via the transfer probe. This particle beam is then well matched to the mass spectrometer requirements. The sample particles are then ionized and mass analyzed by the mass spectrometer.

GC/LC/MS systems provide for broad sample type compatibility with the advantages of mass spectrometry. To make dual use of mass spectrometer components, the GC and LC inputs to the mass spectrometer can be diametrically opposed. A GC/LC/MS system can be operated in a GC mode, when a GC compatible sample is to be analyzed, and in an LC mode, when an LC compatible sample is to be analyzed. To minimize signal noise, it is standard practice to close the LC input when in GC mode, and to close the GC input when in LC mode.

When sample quantities are small, it is important to keep analyte losses to a minimum in the spectrometer. This is true for GC, but especially true for LC, where losses in the mass spectrometer compound losses in the particle beam generator. Furthermore, LC typically yields large molecules that are subject to fragmentation during ionization. This fragmentation distributes what would have been a single peak into multiple smaller peak, reducing signal-to-noise ratio and complicating interpretation of the mass spectrogram. What is needed is a system and method that minimizes this fragmentation and loss of LC analyte in a mass spectrometer.

SUMMARY OF THE INVENTION

The present invention provides for a gas counterflow to an particle beam in a mass spectrometer. In a GC/LC/MS system, a gas counterflow to an LC particle beam can be provided by using the GC system as the counterflow gas source. The counterflow cushions the particle beam, reducing analyte loss and decreasing fragmentation. The increase in signal-to-noise ratio can be enhanced by optimizing the counterflow velocity to between 30 and 50 centimeters per second, and by optimizing the counterflow gas temperature to between 100° C. and 300° C.

The present invention improves signal strength by an order of magnitude. By way of explanation and not of limitation, it is believed that the increased signal strength results from the transfer of thermal energy from the counterflow gas to solvent/analyte clusters in the LC particle beam. This added thermal energy helps desolvate and vaporize these solvent/analyte clusters before they can thermally degrade by contact with a hot metal surface of the ion source. The gas counterflow also reduces the percentage of high momentum analyte particles that exit the source volume before being ionized and focused toward the mass analyzer. These and other features and advantages of the present invention are apparent from the description below with reference to the following drawings.

DESCRIPTION OF THE PREFERRED EMBODIMENTS

Figure 1:
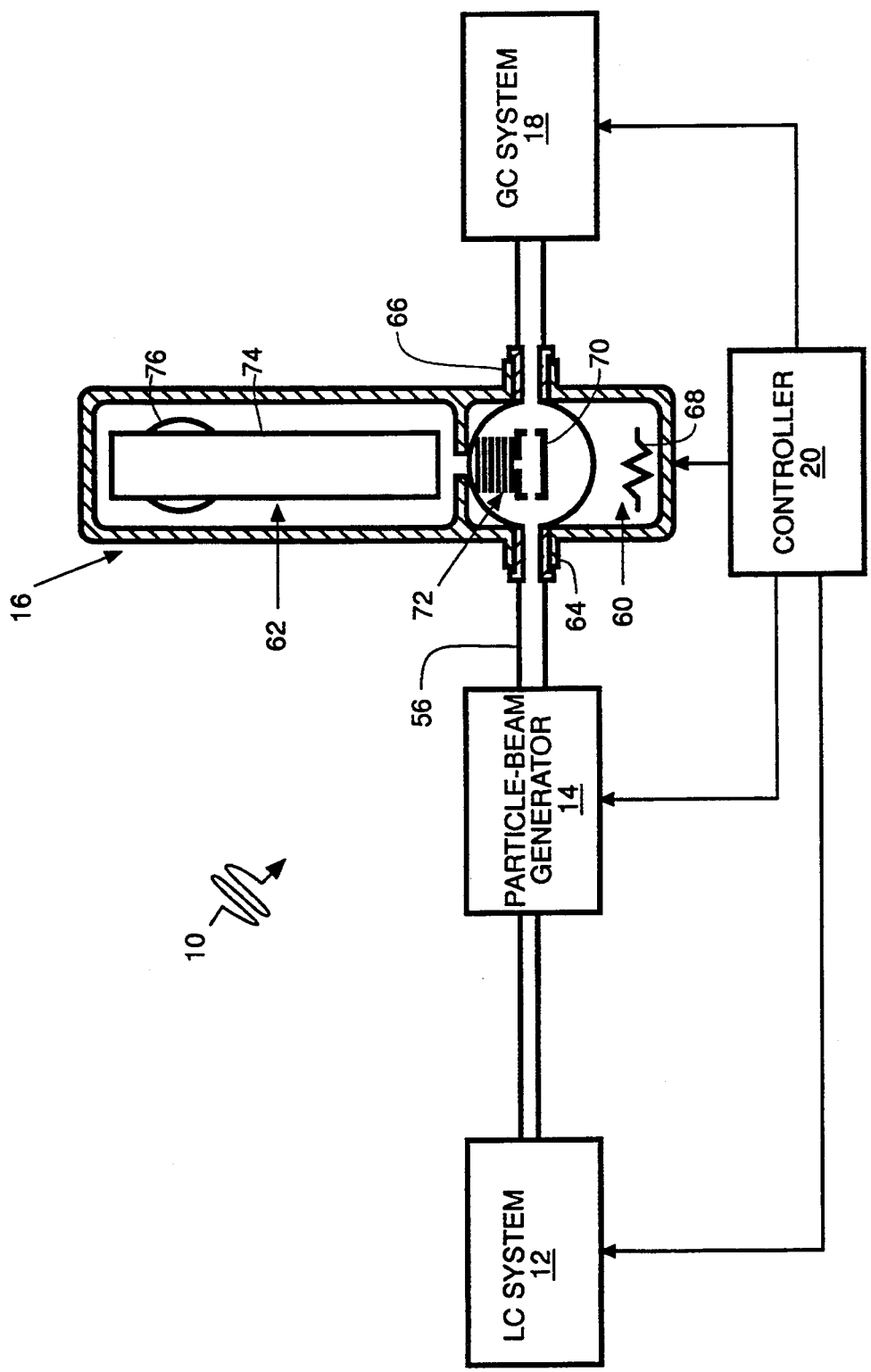
FIG. 1 is a schematic view of a GC/LC/MS system in accordance with the present invention.

A GC/LC/MS system 10 in accordance with the present invention comprises an LC system 12, a particle-beam generator 14, a mass spectrometer 16, a GC system 18 and a controller 20. In an LC mode of system 10, LC system 12 provides an LC effluent to particle-beam generator 14. Particle-beam generator 14 converts the LC effluent to an "LC" particle beam that is directed into mass spectrometer 16. In a GC mode of system 10, GC system 18 provides a GC particle-beam to mass spectrometer 16. Controller 20 coordinates operation of system components to implement the desired mode. The operation of system 10 in its LC mode is described next.

LC system 12 is designed to separate components of a sample mixture in solution. The solvent can be organic or aqueous: aqueous solvents more effectively dissolve polar components, while organic solvents more effectively dissolve nonpolar components. To handle sample, with components having a wide range of polarities, LC system 12 is capable of reverse-phase liquid chromatography in which the solvent gradually changes from an organic solvent to an organic/aqueous solvent mixture to an aqueous solvent. The effluent of LC system 12 is a solvent stream bearing serialized sample components, or "LC analytes".

Figure 2:
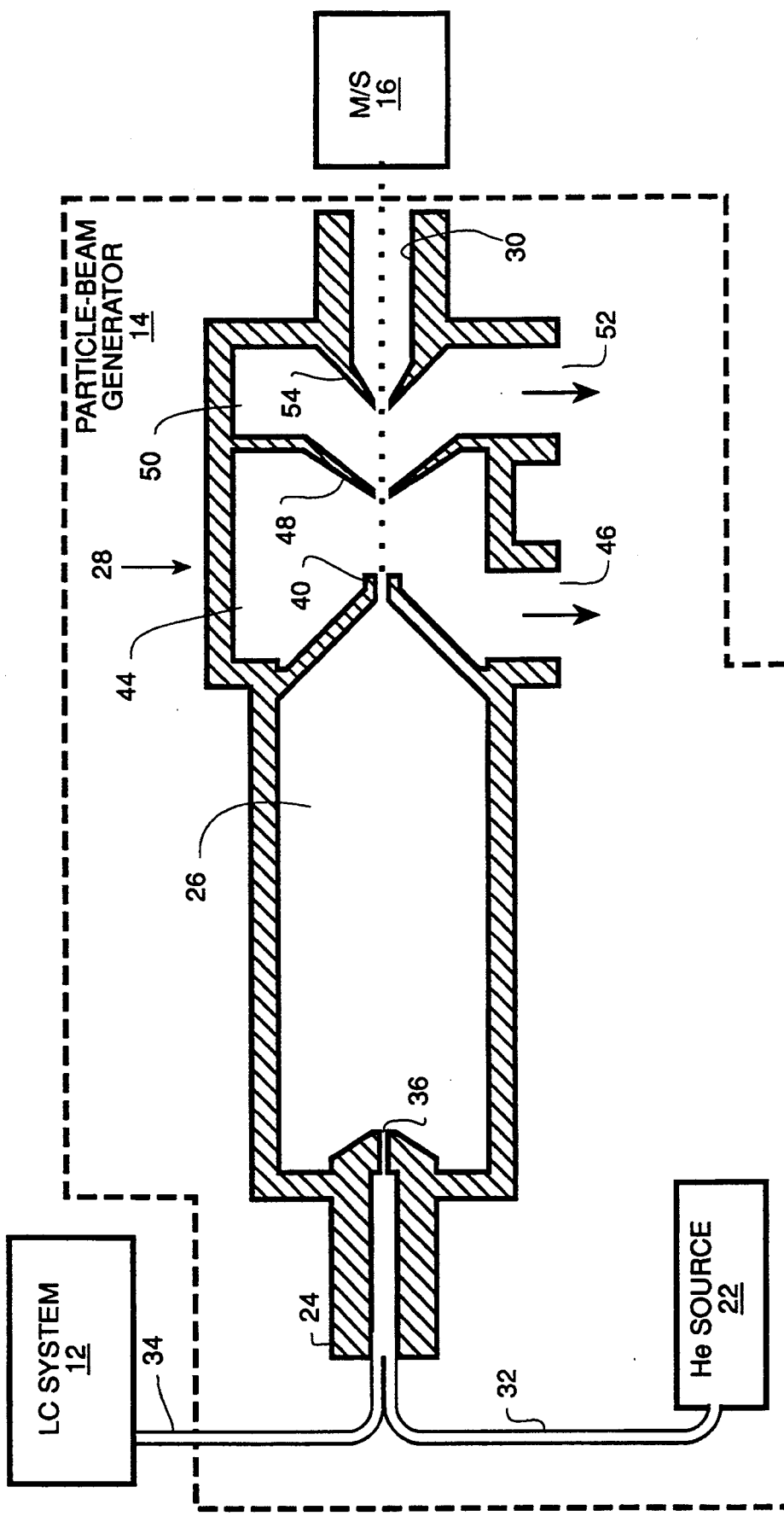
FIG. 2 is a schematic view of a particle-beam generator incorporated in the GC/LC/MS system of FIG. 1.

Particle-beam generator 14 comprises a dispersant-gas source 22, a nebulizer 24, a desolvation chamber 26, a momentum separator 28, and an output bore 30, as shown in FIG. 2. Dispersant-gas source 22 provides a stream of helium under pressure to nebulizer 24 via a conduit 32. Concurrently, effluent from LC system 12 is conveyed to particle-beam generator 14 via a conduit 34. The effluent and dispersant gas contact each other within nebulizer 24. The dispersant gas and the effluent flow through a nozzle 36 of nebulizer 24, so that an aerosol of droplets having a narrow range of diameters enters desolvation chamber 26.

Desolvation chamber 26 is held at close to ambient temperature and pressure. The solvent in the aerosol droplets is vaporized as the droplets transverse desolvation chamber 26 toward its exit jet nozzle 40. What exits nozzle 40 is a mixture of helium, solvent vapor, and analyte particles.

The mixture accelerates toward lower-pressure momentum separator 28. A first stage 44 of momentum separator 28 is maintained at a pressure of about 2–10 torr. Upon entering first stage 44, the mixture is focused into a beam which expands at supersonic speed. The helium and solvent vapor are diverted by a vacuum into a first exhaust 46. The relatively massive analyte particles pass through a central bore in a first stage skimmer 48.

A second stage 50 of momentum separator 28 operates in a similar manner to evacuate the traces of helium and solvent vapor not exhausted by first stage 44. Second stage 50 includes a second-stage exhaust 52 and a second-stage skimmer 54. The vacuum implementing second-stage exhaust 52 maintains a second-stage pressure below 1 torr. The analyte particle beam exiting through an aperture of second-stage skimmer 54 enters output bore 30. From bore 30, the particle beam is directed through a transfer probe 56, FIG. 1, to mass spectrometer 16.

Mass spectrometer 16 includes an ion source 60 and a mass analyzer 62, as shown in FIG. 1. Ion source 60 includes an LC input 64, a GC input 66, a filament 68, an ion focus lens 70, and a lens stack 72. In LC mode, GC system 18 is operated (without a sample) to provide a counter flow gas through GC input 66, which is diametrically opposed to LC input 64. Preferably, the velocity of the counter flow gas is about 41 cm/sec and the temperature of the counter flow gas is about 250° C. This counterflow gas "cushions" the LC particle beam entering LC input 64 to ion source 60.

The LC particle beam diffuses toward mass analyzer 62 due to a pressure drop from ion source 60 to mass analyzer 62. A current through resistive filament 68 causes electrons to be ejected. (Filament 68 is shown out of place in FIG. 1; it actually is above the page, over ion focus lens 70.) The electrons bombard the LC particle beam, ionizing analyte molecules. The resulting ion beam is conditioned by lens stack 72 and directed by pressure differential into mass analyzer 62. Mass analyzer 62 includes a quadrupole mass filter 74 and an electron multiplier 76. Mass filter 74 selects a particular charge-to-mass ratio to reach and be detected by multiplier 76.

Mass filter 74 is swept so that the detected charge-to-mass ratio changes in time. Thus, the recorded output of electron multiplier 76 is a mass spectrum in which analyte concentration is plotted as a function of charge-to-mass ratio. The location of peaks can be used to identify analytes, while peak areas can be used to determine analyte concentrations.

Figure 3:
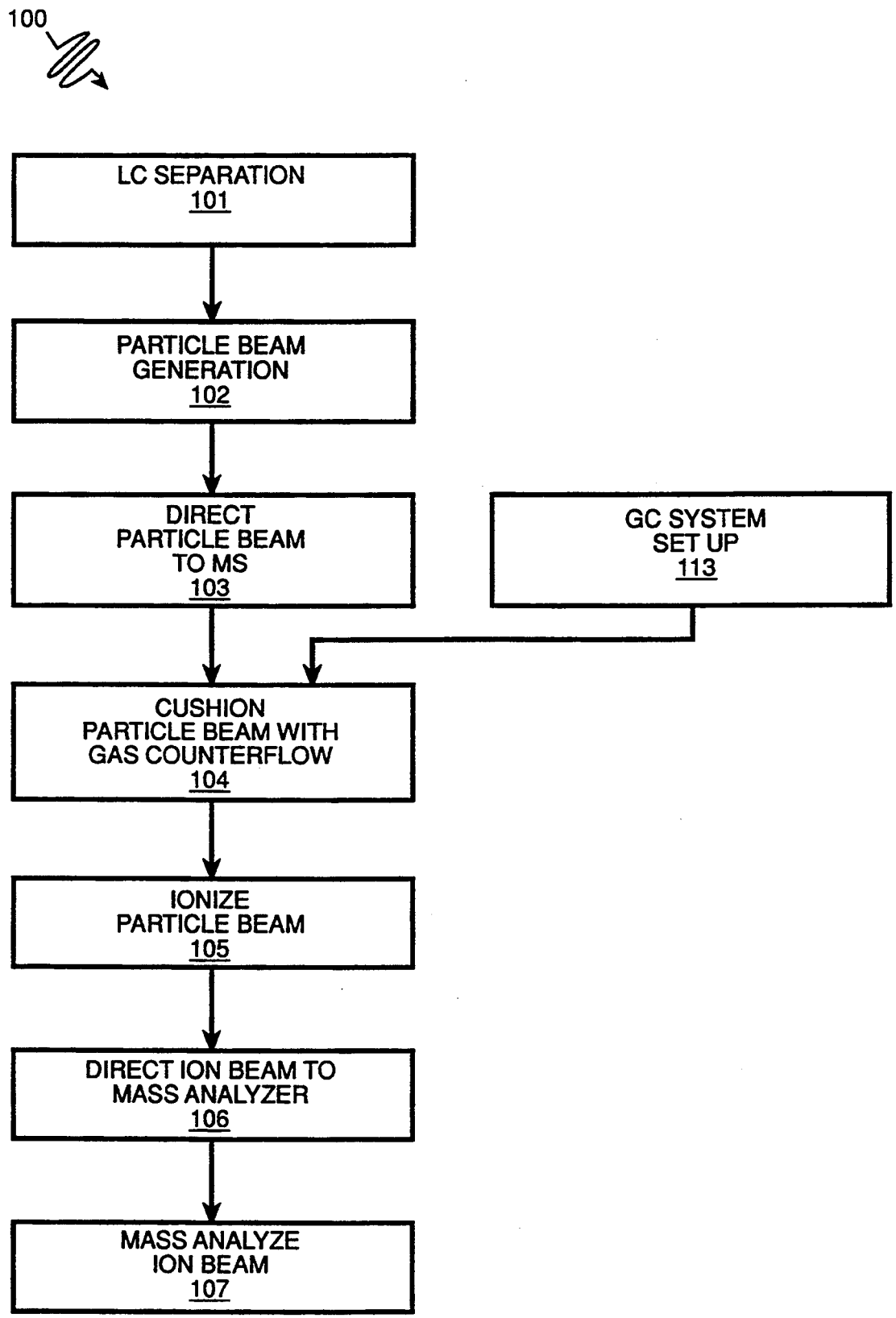
FIG. 3 is a flow chart of a MS method employed in the GC/LC/MS system of FIG. 1 in accordance with the present invention.

The method 100 of LC mode operation of system 10 is flow charted in FIG. 3. At step 101, LC system 12 is operated to yield an LC effluent. At step 102, the LC effluent is converted to a particle beam by particle-beam generator 14. At step 103, the particle beam is directed into mass spectrometer 16.

At step 104, the particle beam is cushioned by a gas counterflow. Preparation for step 104 is indicated at step 113, which involves setting up GC system 18 (without a GC sample) so that the gas counterflow arrives by the time the particle beam enters mass spectrometer 16.

Step 113 can involve adjusting the counterflow velocity to between 30 and 50 cm/sec, preferably to about 41 cm/sec, and adjusting a GC oven of GC system 18 so that the counterflow gas temperature is between 100° C. and 300° C., preferably at about 250° C.

At step 105, the cushioned particle beam is ionized. At step 106, the resulting ion beam is conditioned and directed into mass analyzer 62. At step 107, the ion beam is mass analyzed to yield a mass spectrum. Mass analysis includes substeps of mass filtering and ion detection.

GC mode operation of system 10 is conventional. LC system 12 and particle-beam generator 14 are operationally decoupled from mass spectrometer by closing a valve along transfer probe 60. (In theory, particle-beam generator could be operated to provide a cushion for the GC particle beam.) The GC oven is adjusted to vaporize a GC sample. The resulting vapors are swept along a GC column by the carrier gas (which is the same as the counterflow gas, e.g., helium). The GC sample components partition between the carrier gas and the solid support, causing GC sample components to serialize. The serialized components then enter mass spectrometer through GC input 64. The components are then ionized and mass analyzed.

EXAMPLE I

The LC system was used to separate components of a sulfonylurea herbicide using an aqueous solvent. Initially, the GC system was left in the MS interface with a GC column temperature of 50° C., a column head pressure of 5 psig, and a gas velocity of 25 cm/sec. Upon increasing the linear velocity, a sharp increase in signal strength was observed. The increase leveled out at 41 cm/sec. At this velocity, signal strength had increased five-fold over what it was at 25 cm/sec.

With the linear velocity maintained at 41 cm/sec, GC oven temperature, and therefore counterflow temperature, was increased. Signal strength increased with temperature, leveling out at 250° C. The signal strength at 41 cm/sec and 250° C. was ten-fold over what it was at 25 cm/sec and 50° C. When the linear velocity and/or temperature was decreased, signal strength decreased as well.

Without the counterflow, the electron impact spectra of sulfonylurea herbicides contains four or more characteristic fragment ions and no molecular ions. The base peak was 136 atomic mass units (amu), representing sulfonanaide $CH_3CN*H_2O$ complex. A 155 amu ion is the triazine isocyanate. A 221 amu ion is the triazine amine. A 280 amu ion is the sulfonamide urea. The relative ratio is 100, 50, 40, and 20 respectively.

As the counterflow was introduced, and its velocity and temperature were raised, the fragmentation there "softened". The 136 amu fragment essentially disappeared, leaving 221 amu as the base peak. A small amount of molecular ion (387 amu) was also apparent in the enhanced spectrum, further indicating reduced fragmentation.

EXAMPLE II

The foregoing procedures were applied to sucrose instead of sulfonylurea herbicide. Sensitivity increased, but fragmentation was not reduced (since sucrose does not fragment).

While the foregoing description concerns an GC/LC/MS system, it is apparent that the present invention would apply whatever the source of the particle beam and whatever the source of the counterflow gas. Accordingly, the present invention provides for alternative particle-beam sources and alternative counterflow gas sources. These and other modifications to and variations upon the preferred embodiments are provided for by the present invention, the scope of which is limited only by the following claims.

What is claimed is:

1. A method of analyzing an initially non-ionized particle beam, said method comprising the steps of:
   generating an initially non-ionized particle beam;
   flowing gas counter to said particle beam while said particle beam is non-ionized;
   ionizing said non-ionized particle beam so that it becomes an ionized particle beam;
   directing said ionized particle beam into a mass analyzer; and
   mass analyzing said ionized particle beam.

2. A method of operating a GC/LC/MS system in LC mode, said GC/LC/MS system including a GC subsystem capable of providing a GC carrier gas flow, said method comprising the steps of:
   generating an LC effluent;
   generating an initially non-ionized particle beam from said LC effluent;
   directing said non-ionized particle beam into a mass spectrometer;
   flowing said GC carrier gas into said mass spectrometer and counter to said non-ionized particle beam;
   ionizing said particle beam so that it becomes an ionized particle beam;
   directing said ionized particle beam into a mass analyzer; and
   mass analyzing said ionized particle beam.

3. A method as recited in claim 2 wherein in said operating step, said GC carrier gas has a flow velocity between 30 and 50 cm/sec.

4. A method as recited in claim 2 wherein in said operating step, said GC carrier gas has a temperature between 100° C. and 300° C.

5. A method as recited in claim 2 wherein said effluent is aqueous.

6. An analytical system comprising:
   a particle-beam generator for providing an initially non-ionized particle beam having analyte particles;
   a mass spectrometer for analyzing an ionized particle beam, said mass spectrometer including
      a particle beam input coupled to said particle-beam generator for receiving said non-ionized particle beam;
      an ionizer for ionizing said non-ionized particle beam so that it becomes an ionized particle beam having analyte ions, and
      a mass analyzer for separating said ions of said ionized particle beam at least partially as a function of mass,
   a counter-flow gas source for providing a gas flow counter to said non-ionized particle beam at said ionizer; and
   a controller coupled to said counter-flow gas source for causing said gas flow while said mass spectrometer is receiving said ionized particle beam.

7. An analytical system as recited in claim 6 further characterized in that:
   said analytical system further comprises an LC system coupled to said particle-beam generator for providing an effluent thereto, said effluent including LC analyte and solvent, said particle-beam generator including
  a nebulizer for nebulizing said effluent into droplets containing LC analyte and solvent, said nebulizer including a gas source for providing a nebulizer gas for assisting in said nebulizing,
  a desolvation chamber for desolvating said droplets to form a mixture of LC analyte particles, solvent vapor, and nebulizer gas, and
  a separator for separating said solvent vapor and said nebulizer gas from said analyte particles to form said particle beam;
said counter-flow gas source being a GC system;
said mass spectrometer further including a GC input coupled to said GC system and through which said gas flow enters said mass spectrometer, said ionizer providing for ionization of said GC analyte;
said controller providing for GC and LC modes of operation,
  when said analytical system is in its GC mode, said controller causes said GC system to produce a GC beam with GC analyte carried by said gas flow,
  when said analytical system is in its LC mode, said controller causes said GC system to produce said gas flow without GC analyte.

* * * * *